Figure 9:
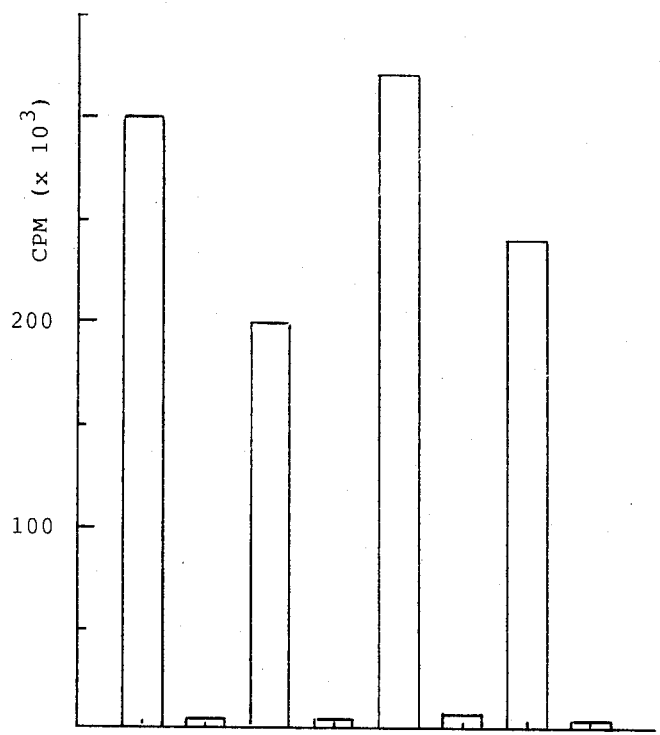

United States Patent [19]

De Baetselier

[11] Patent Number: 4,737,455

[45] Date of Patent: Apr. 12, 1988

[54] ANALYTICAL UTILIZATION OF PHAGOCYTE CELL LINES

[75] Inventor: Patrick De Baetselier, Berchem, Belgium

[73] Assignee: 501 N.V. Innogenetics, Gent, Belgium

[21] Appl. No.: 723,100

[22] Filed: Apr. 15, 1985

[30] Foreign Application Priority Data

Apr. 16, 1984 [NL] Netherlands .................. 8401221

[51] Int. Cl.$^4$ .................. C12N 5/00; C12Q 1/02; G01N 33/567; G01N 33/569
[52] U.S. Cl. .................. 435/7; 435/29; 435/172.2; 435/240.26; 435/941; 436/63; 436/172; 436/503; 436/519; 436/821; 935/90; 935/103; 935/110
[58] Field of Search .................. 435/29, 172.2, 948, 435/7, 240.26; 436/63, 172, 503, 519, 821; 935/90, 103, 110

[56] References Cited

U.S. PATENT DOCUMENTS 4,064,007 12/1977 Choay et al. .................. 435/240

FOREIGN PATENT DOCUMENTS 0118917 9/1984 European Pat. Off. ............. 435/240

OTHER PUBLICATIONS

S. Gordon et al., *Chemical Abstracts*, 75, 149438e, 1971.
E. Tzehoval et al., *Journ. Immunology*, 132, 1741–1747, 1984.
C. S. F. Easmon et al., *Immunology* 41, 67–74, 1980.
V. G. Hemming et al., *Journ. Clin. Invest.* 58, 1379–1387, 1976.
C. R. Johnson et al., *Journ. Immunol. Meth.* 67, 108–117, 1984.
P. Stahl et al., *Journ. Cell Biol.* 93, 49–56, 1982.
E. Tzehoval et al., In S. J. Norman et al. (Eds.) *Macrophages and Natural Killer Cells*, Plenum Press, New York, pp. 445–451, 1982.

*Primary Examiner*—Sidney Marantz
*Assistant Examiner*—David A. Saunders
*Attorney, Agent, or Firm*—Webb, Burden, Robinson & Webb

[57] ABSTRACT

The property of phagocyte cells to show chemiluminescence when activated by certain chemical or immunological agents is used for a qualitative and quantitative analysis of such agents in biological fluids. A variety of factors such as opsonizing anti-bodies, complement, inhibitors, membrane-specific anti-bodies, and their antigens, membrane-specific lectins, lymphokines, endotoxins, toxic substances and others can be analyzed in this way. The new method finds application in the biotechnical, clinical, immunological and pharmacological fields, with a special preference for toxicological screening of pharmaceuticals. The phagocyte cells needed for the analysis can be derived from a continuous phagocyte cell line and a method of producing such a cell line is provided.

25 Claims, 7 Drawing Sheets

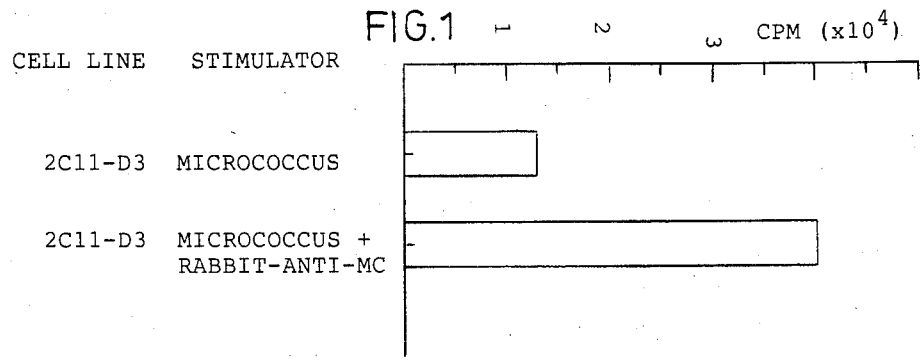
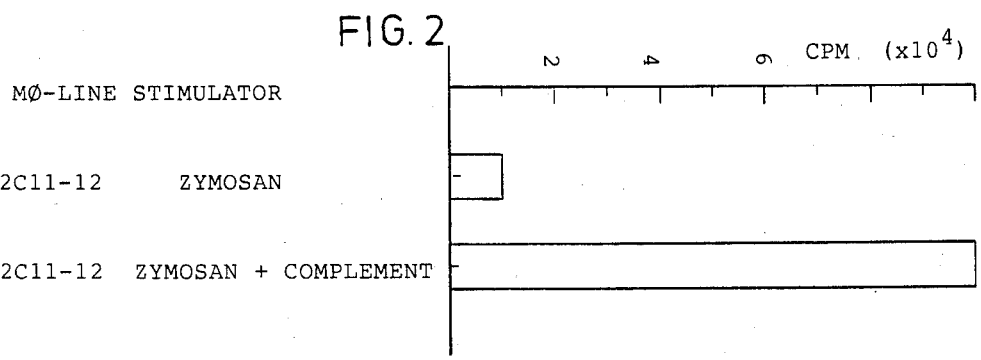
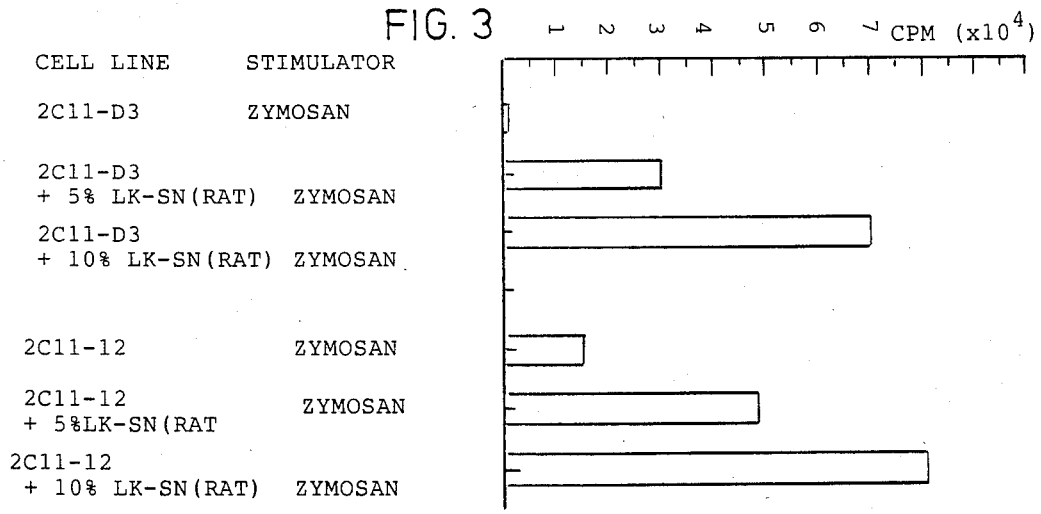

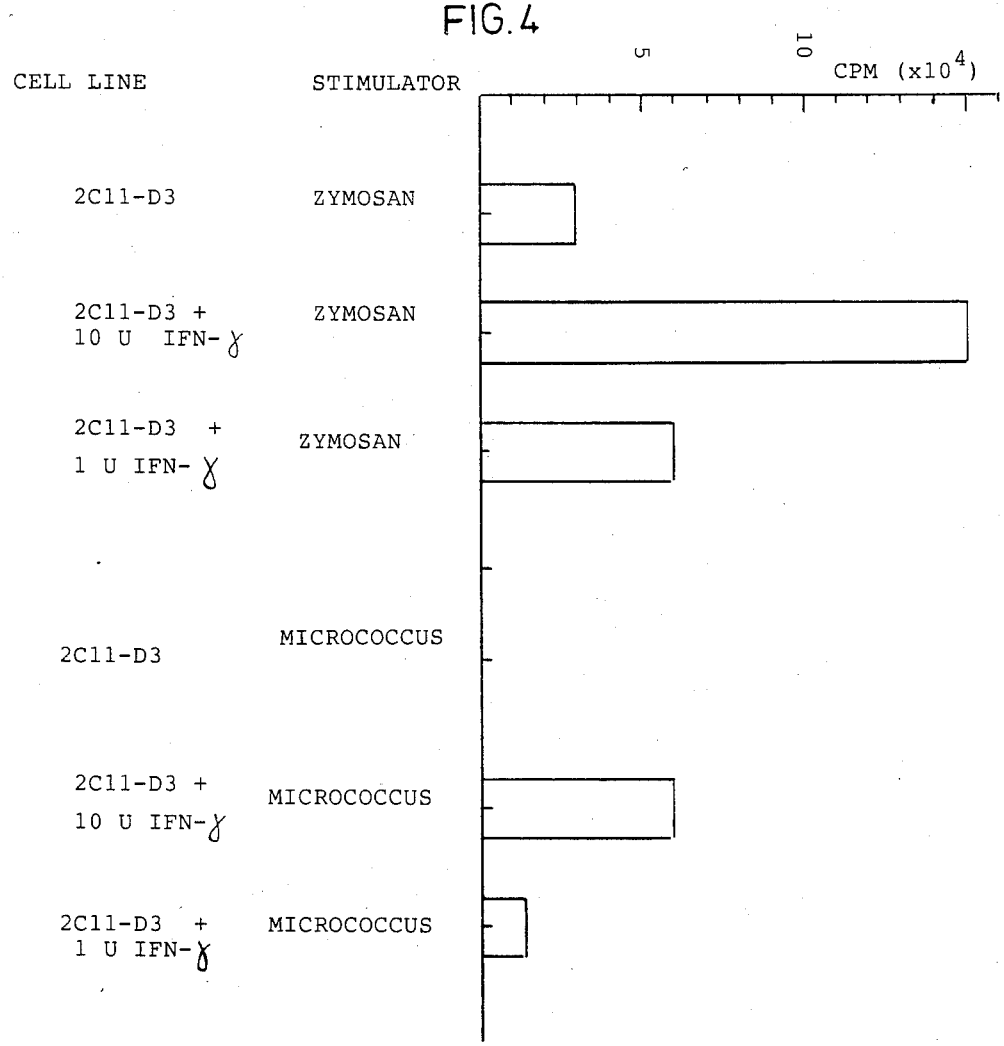

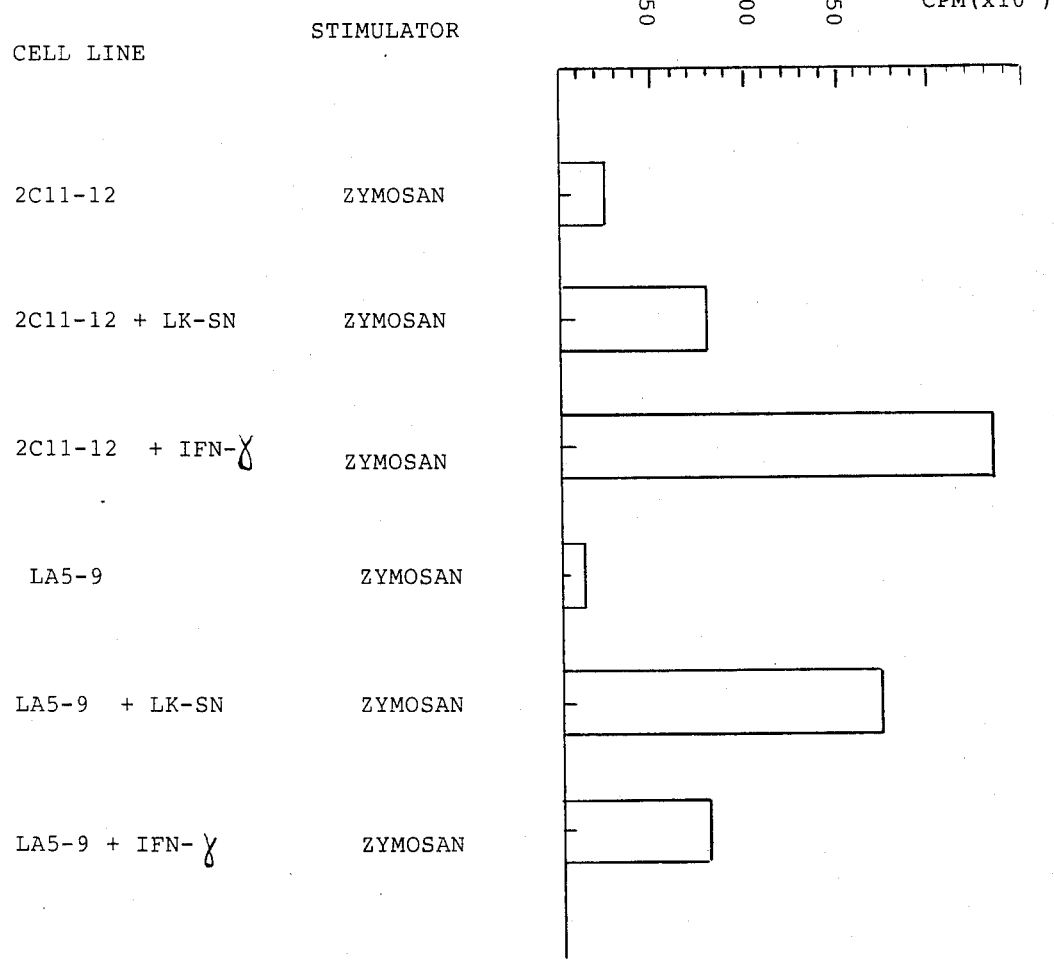

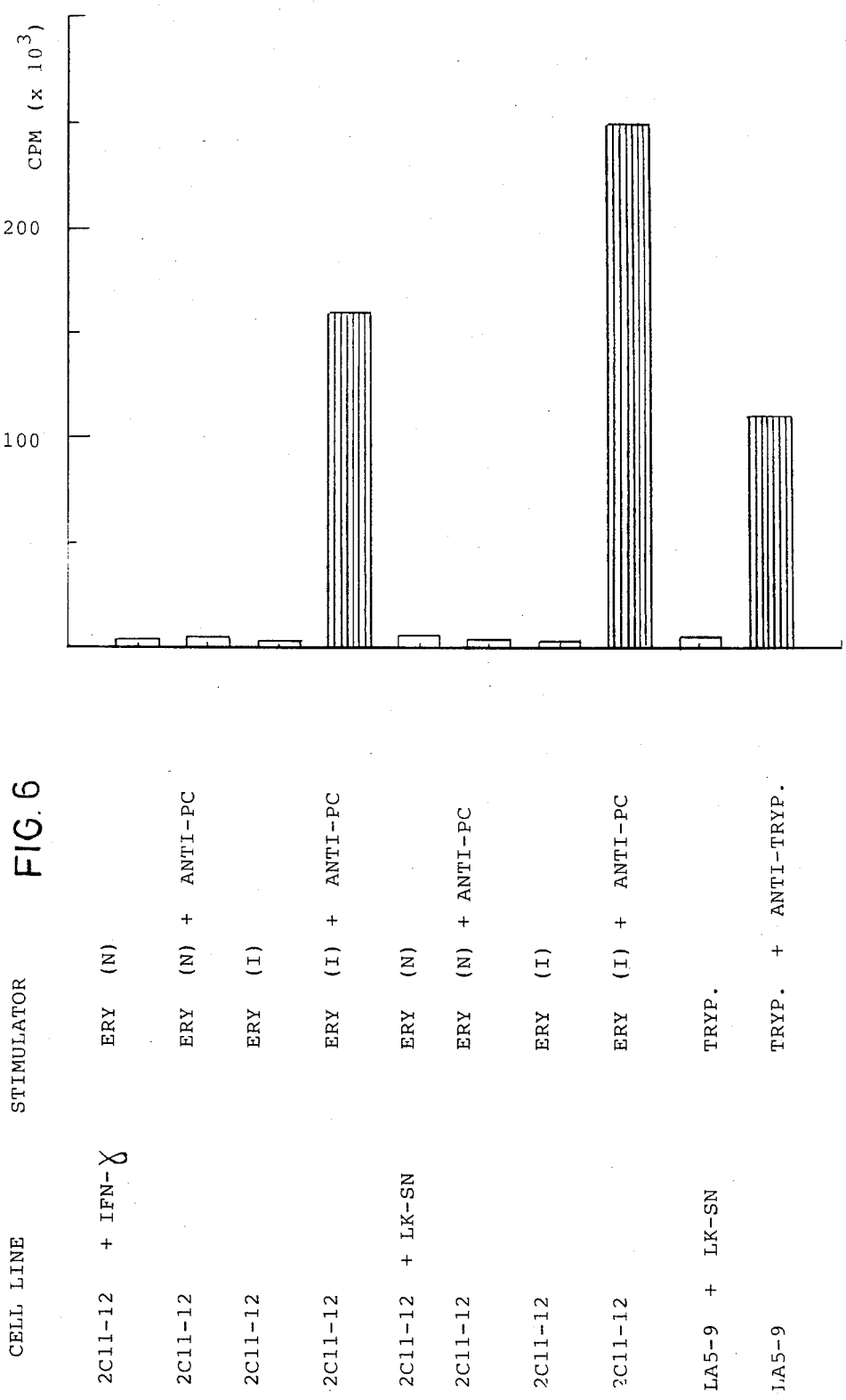

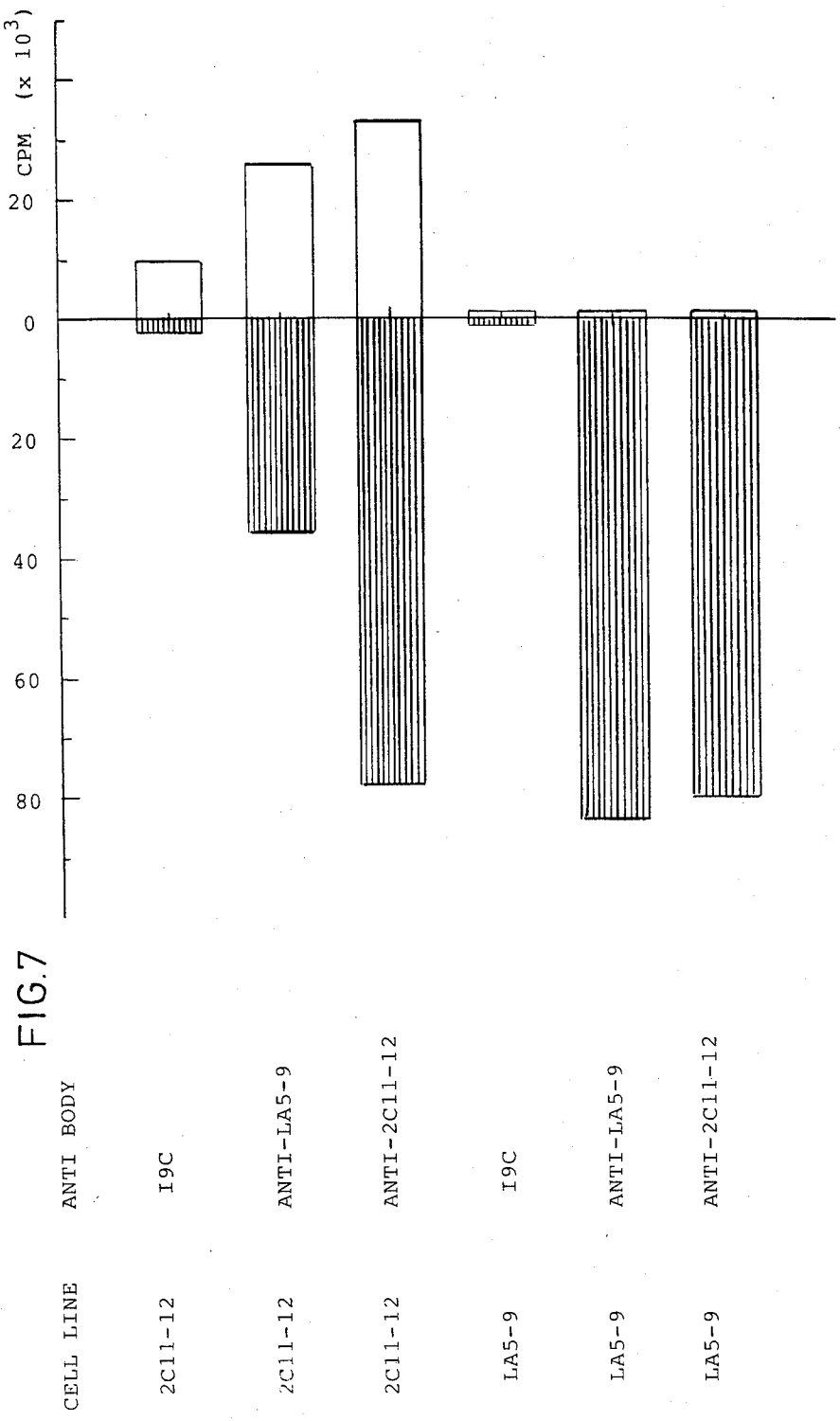

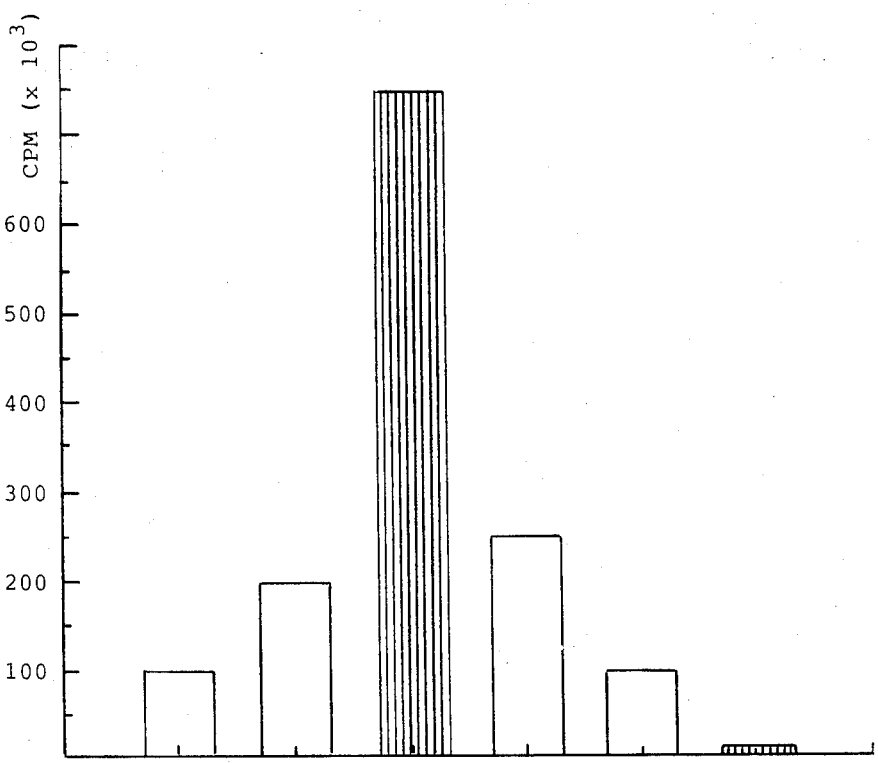

ANALYTICAL UTILIZATION OF PHAGOCYTE CELL LINES

This invention relates to the analysis of biological fluids, especially for biotechnical, clinical, immunological and pharmacological search, thereby utilising phagocyte cells belonging to a continuous phagocyte cell line.

Phagocytes are cells occurring in the human and animal organism and capable of absorbing and digesting microscopic particles. Among them, some types of white blood cells such as macrophages, neutrophilic leukocytes and monocytes which take a part in the defense against bacterial infections are especially important.

It is known that phagocytes in cell suspension may be activated by chemical or immunological agents, thereby inducing chemiluminescence. This chemiluminescence is probably linked to the formation of unstable oxygen compounds such as superoxide, anions, atomic oxygen and hydrogen peroxide, which pass into a more stable form under emission of light. The light emission may be intensified by the addition of luminescent substrates such as luminol and lucigenin and may be measured with the aid of suitable apparatus. Thereupon, the measurements may be used to determine the activity of the phagocytes in a biological fluid in order to investigate possible immunological deficiencies in that fluid.

In accordance with the invention, however, the chemiluminescence of activated phagocytes is used for another purpose, viz. to investigate the presence and proportion of several agents in biological fluids. Such agents may be immunological factors taking a part in the defence mechanism against antigens but they also may be chemical agents such as undesired toxic substances that have to be detected or pharmaceuticals whose toxicity should be determined. Thereby, use is always made of the fact that such agents have a stimulating or modulating influence on the activation of the phagocyte cells.

A precondition for the analytical utilisation of phagocyte cells is that such phagocyte cells have uniform properties, that they are available in sufficient amount for analytical utilisation and that they can be dosed well. The normal phagocytes isolated from a human or animal organism do not satisfy this precondition because they are extremely heterogeneous, show many stages of differentiation and do not have the capability to be cultivated in cell cultures. Therefore, the invention should first provide a phagocyte cell line of standardised characteristics which ca be cultivated in a continuous way and which can be utilised well for the chemiluminescence tests.

The invention has for its object to provide continuous phagocyte cell lines having standardised characteristics, as well as a method for the preparation thereof.

Further, the invention has for its object to provide a method for the analysis of biological fluids such as blood, blood serum and the like, such method serving to determine a plurality of immunological and chemical factors, in a qualitative as well as a quantitative way.

A further object is to find new methods for biotechnical, clinical, immunological and pharmacological (especially toxicological) research on the basis of the preceding.

Further objects of the invention will be apparent from the further description.

Continuous phagocyte cell lines

The invention provides in the first place continuous phagocyte cell lines which have functional phagocyte characteristics and the capacity of continuous proliferation. Such cell lines have standardized properties, are suitable for continuous cultivation, are thereby always available for analytical utilisation and may be dosed well during that utilisation.

The term "functional phagocyte characteristics" may comprise several characteristics such as phagocytosis, chemiluminescence, secretion of lymphokines and enzymes, tumoricidal activity and the like. It is unnecessary for the continuous phagocyte cell lines to have all these characteristics at the same time or all characteristics in the same degree although it may be desirable for later analytical utilisation that the chemiluminescence characteristic is present in a certain degree.

In accordance with the invention, the continuous phagocyte cell lines may be prepared by a hybridization technique comprising a cell fusion of phagocytes with suitable tumor cells followed by cloning and selection of the resulting hydrids. The selected and further cultivated hydrid cells will have functional characteristics of the tumor cells then (viz. continuous proliferation in vivo and in vitro) as well as functional characteristics of the phagocyte cells such as e.g. phagocytosis, chemiluminescence and the like. By means of appropriate selection, it is possible to arrive at cell lines which have certain functional characteristics in a greater or lesser degree and also to arrive at cell lines which react specifically or less specifically to certain agents at will.

The phagocyte cells to be used for this hybridization technique may comprise macrophages, neutrophilic leukocytes or monocytes, although macrophages are preferred. They may isolated from several organs of the human or animal organism, whether or not after previous stimulation of the organism with suitable agents. Thus, the presence of macrophages in the abdominal membrane may sometimes be induced by a previous injection of lectin, endotoxine, thioglycolate and the like. The harvested phagocyte cells should be separated from impurities (e.g. lymphoid cells) which may be effected with advantage by utilising the property of phagocyte cells (in contradiction to other cells) to adhere well to glass and plastics. Subsequent to such a separation, the phagocyte cells may be used directly for cell fusion.

Tumor cells are used as another component for cell fusion. In order to get satisfactory results, these tumor cells should resemble the phagocyte cells phenotypically which means that macrophage-like human tumor cells are preferably used for hybridization with human macrophages and that macrophage-like tumor cells from mice are preferably used for hybridization with murine macrophages. Further, the tumor cells should be fusogenic, that is they should have the capacity of entering easily into a cell fusion. The tumor cells belong preferably to a continuous cell line of well-known characteristics.

It may be advantageous to cultivate beforehand a variant or mutant being sensible for certain chemicals such as certain purines bases, from such a tumor cell line. If e.g. a mutant is cultivated which is resistant to 8-azaguanine, but sensible to HAT-medium (a medium comprising hypoxanthine, aminopterine and thymidine) this HAT-medium may be used later on after cell fusion to destroy unfused cells.

Cell fusion may be effected in a conventional way, e.g. by combining the phagocyte cells and the tumor cells in a polyethylene glycol-comprising medium of suitable temperature (e.g. 37° C.). The possibilities of cell contact between both types of cells and consequently the chances of cell fusion may be increased by agitation. The time period of this treatment is more or less critical and will normally be about 2 minutes because the chances of cell fusion are reduced at shorter contact durations and the polyethylene glycol will be toxic for the cells at longer contact durations. After completion of the cell fusion, the cells are transmitted from the fusion medium to another medium and unfused cells are destroyed by the addition of suitable chemicals e.g. a HAT-medium. Only fused cells (hybrid cells) will remain in this way. Thereafter the conventional treatments of cloning (incl. subcloning) and selecting the hybrid cells can follow.

Cloning and subcloning may be effected on Microtiter ® plates or an agar in a Petri-dish ("Microtiter ®" is a registered trademark of Dynatech Laboratories.). Any suitable culturing medium for cell culture or tissue culture may be used for cultivating the hybrid cells. A preferred medium in RPMI 1640 (Gibco, Grand Island, N.Y., USA), to which 10% of fetal calf serum (Gibco), 2 mM of glutamine, 100 U/ml of penicillin and 100 mu/ml of streptomycin has been added. The medium RPMI 1640 (developed by the Roswell Park Memorial Institute) comprises inorganic salts (Nacl, $NaHCO_3$, $Na_2HPO_4$, etc.), glucose, several amino acids and several vitamins. In the following description the term "culture medium" always denotes RPMI 1640 with the aforesaid additives unless indicated otherwise. The selection of hybrid cells is effected on the basis of their functional chacteristics which may be determined by means of tests. In general, many characteristics including phagocyte and tumor characteristics may be determined. Typical examples of phagocyte characteristics are: phagocytosis (of red blood cells, bacteria, yeast cells, parasites etc.), chemiluminescence (after stimulation by yeast extracts, bacteria, parasites, phorbol esters, tumor cells etc.), secretion of lumphokines, endotoxins, phorbol esters etc. An example of specific tumor characteristics is formed by the continuous proliferation of the cells in vitro and in vivo.

Several characteristics, dependent from the intended utilisation, may be used as a criterion for the selection of hybrid cells. Thus, e.g., hybrid cells showing a strong chemiluminescence under influence of certain stimulating agents may be selected if it is desired to detect such stimulating agents lateron in biological fluids. As an alternative, it is possible to select hybrid cells which show only a minor degree of chemiluminescence under influence of a stimulating agent and which have an intensified chemiluminescence under influence of a stimulating agent plus a modulating agent. In that case, the hybrid cells may serve later on to detect a modulating agent in biological fluids. Many other selection criteria are possible in addition thereto.

The selected hybrid cells are further cultured in a suitable culture medium, e.g. said RPMI medium with additives and will form a continuous cell line then. Cells for analytical utilisation may be derived from this continuous cell line at any time. Prior to utilisation, the cell lines are preferably frozen in liquid nitrogen after the addition of 10 vol.% of dimethylsulfoxide to the culture medium.

The preparation of the continuous phagocyte cell lines is illustrated by the following, non-restricting example. Although murine macrophages and tumor cells are exclusively mentioned therein, it will be clear that phagocyte cell lines of human origin can be prepared in the same way and will lead to equivalent analytical utilisations.

EXAMPLE 1

Preparation of continuous phagocyte cell lines

A number of continuous phagocyte cells lines was prepared by cell fusion of murine macrophages and suitble murine tumor cells, followed by cloning, subcloning and selecting the resulting hybrid cells.

Isolation of macrophages

Macrophages were isolated from the spleen or the peritoneum of mice, the mice in the latter case being inoculated with lectin (Concanavaline A, Sigma Corporation) three days beforehand. The macrophages were freed from contaminating lymphoid cells by transmitting them to a Petri-dish containing culture medium where they adhered to the bottom of the dish. After removal of the culture medium followed by rinsing, the adhering macrophages were carefully scraped from the Petri-dish; they were ready then for cell fusion.

Tumor cell line

The tumor cell line as used herein was derived from murine lymphosarcoma J774. This tumor J774 developed in 1968 in a single mouse of the strain BALB/c during a plasmacytoma induction program in the National Institute of Health, USA (compare J. Immunol. 107, 927, 1971). A cell line J.774.2 has been derived from a cell culture of tumor J774 and is available at the Albert Einstein College of Medicine, Bronx, N.Y., USA.

The cell line J774.2 was cultivated further in a medium containing 25 mM of 8-azaquanine in order to find a variant which was resistant to azaguanine. After several fresh inoculations in the same medium, a mutant indicated as C2E2-HAT was obtained, which was resistant to azaguanine and sensible to HAT-medium. This cell line C2E2-HAT was used as a fusion partner for the murine macrophages.

Generation of hybrid cells

In a test tube containing 1 ml polyethyleneglycol (molecular weight 1500, 50% in PBS, i.e. a phosphate-buffered physiological saline solution) $10^7$ macrophage cells were mixed at 37° C. with $10^6$ tumor cells and agitated for 2 minutes. Thereafter, the cell suspension was slowly diluted with culture medium (RPMI 1640 with additives) to reach a final volume of 8 ml and then centrifuged at 1800 RPM. The harvested cells were suspended in HAT-medium and distributed over the wells of a 96-well microtiter plate. The plate was incubated at 37° C. in a 5% $CO_2$ containing humid atmosphere. From day 10, the wells in the plate were observed carefully with a phase-contrast microscope. Hybrid colonies were visible after 20–30 days whereupon some cells thereof were transmitted to Petri-dishes filled with culture medium and were tested on functional characteristics. Hybrid cells from those colonies that showed manifest macrophage characteristics were distributed for subcloning over agar plates (0.33% Difco agar in culture medium) and cultured thereon. Visible colonies appeared after 10–20 days and were transmitted to culture medium-containing plates and further cultured thereon, each time at 37° C. and in a 5% $CO_2$ humid atmosphere. As soon as a sufficient amount of cells had been formed, they were tested on functional characteristics. On the basis of these tests a certain number of colonies was selected for subsequent utilisation. They were cultured further as a continuous cell line by regular fresh inoculation in culture medium and in a few cases they were stored by freezing them at −70° C.

Tests on functional characteristics

In order to determine the characteristics of the resulting hybrids, samples thereof were subjected to the following tests, prior to or after cloning in agar.

Determination of Fc-receptor positions

This test was effected by bonding IgG-coated erythrocytes to the membrane of the hybrid macrophage cells. Approximately $5 \times 10^5$ cells were transmitted to a microscope slide and covered with a suspension of IgG-coated erythrocytes. After 30 minutes at 37° C., the slide was rinsed with culture medium and the number of rosette-forming cells was observed. A cell was considered positive when three or more erythrocytes were found on it.

Phagocytosis

For this test, the same method was used as for determining the Fc-receptor positions. After contacting the cells with IgG-coated erythrocytes for 30 minutes, the red blood cells absorbed to the exterior were dissolved by dipping in distilled water for ten seconds. After rinsing with culture medium, the hydrid macrophage cells were observed under a microscope and the number of erythrocytes ingested by each cell was investigated.

The phagocytic activity was also determined by ingestion of other particles, such as fluorescent bacteria, fluorescent plasmodia and yeast cells.

Lysozyme secretion

Culture fluids of the hybrid cells were added to holes in an agar plate, containing 1 percent agar and 1 percent particles of Micrococcus luteus. Halo formation around a hole was considered as an indication for active secretion of lysozyme.

Secretion of interleukine-1

This characteristic was tested by microscopic evaluation of the capacity of a culture fluid from the hybrid cells to induce the proliferation of murine thymocytes in the presence of a stimulating substance, viz. phytohaemagglutine (PHA, a plantlectin from Difco).

Chemiluminescence

Light emission by chemiluminescence was tested as described in the other examples. An opsonized yeast extract (Zynosan, Difco) or opsonized micrococci were used as a stimulating agent, whereas a lymphokine-containing culture fluid or an endotoxin composition (Lipopolysaccharide, Difco) was used as a modulating agent.

Results

Some of the resulting cell lines and their characteristics are summarized in table I. The cell lines belonged to three fusion experiments utilizing tumor cells of the cell line C2E2-HAT. The macrophages in experiments 1 and 2 were derived from the spleen cells of a BALB/C-mouse and the macrophages in experiment 3 were derived from the peritoneum of a CBA-mouse after a previous lectin injection.

The following characteristics were tested:
Fc Fc-receptor positions
Phago Phagocytosis
Lys Secretion of lysozyme
IL-1 Secretion of Interleukine-1
CL Chemiluminescence with stimulating agent
CL+MO Chemiluminescence with stimulating and modulating agents The following scale has been used for evaluating the various characteristics:
+Strong
±Moderate
−Weak For the chemiluminescence characteristics, they will correspond approximately with a maximum light intensity per $2.10^4$ cells of:
+ >100.000 photons/min.
± ca. 40.000 photons/min.
− <1000 photons/min.

TABLE I

| Fusion Exp. | | Code No. | Fc | Phago | Lys | IL-1 | CL | CL + MO |
|---|---|---|---|---|---|---|---|---|
| 1 | clone | 2C11 | + | + | + | + | ± | + |
| | sub clones | 2C11-12 | + | + | + | + | ± | + |
| | | 2C11-D3 | + | − | + | − | − | + |
| | | 2C11-11 | + | + | + | − | ± | + |
| | | 2C11-3 | + | + | + | + | ± | + |
| 2 | clone | LA5 | + | + | + | + | ± | + |
| | sub clone | LA5-9 | + | + | + | + | ± | + |
| 3 | clone | C4 | + | + | + | − | − | + |
| | sub clones | C4-2 | + | + | + | − | − | + |
| | | C4-5 | + | + | + | − | − | + |
| | | C4-10 | + | + | + | − | − | + |

From the table, it can be seen that all selected cell lines had a significant contrast in chemiluminescence characteristics (CL and CL+MO). The cell lines from groups 2C11 and LA5 have been used for analytical experiments (compare examples 2–10).

Analytical utilisations

In accordance with the invention, the phagocyte cell lines described above can be used for several analytical utilisations especially with biological fluids.

Thus, the invention provides a method of analyzing biological fluids which comprises the steps of providing hybrid phagocyte cells belonging to a continuous cell line, treating the hybrid phagocyte cells with a fluid to be analyzed and measuring the chemiluminescence of the phagocyte cells thus treated in order to determine phagocyte-stimulating and/or phagocyte modulating factors in the fluid under analysis.

This analysis is based upon the above-mentioned phenomenon that phagocyte cells may be activated by certain agents and may be induced to emit light (chemiluminescence). This phenomenon will also occur in the cells of a continuous phagocyte cell line provided that the selection of hybrid cells for the continuous cell line has been carried out such that the chemiluminescence characteristic is still present. The strength of the emitted light can be measured with suitable apparatus and will form an indication for the presence of stimulating and/or modulating factors in the fluid under analysis.

In this analysis, it is useful to have a basis of comparison. Therefore, it is preferred to carry out a control test, thereby measuring the chemiluminescence of phagocyte cells which have not been treated by the fluid to be analyzed, and to compare the measured results of control tests and actual test in order to determine the said stimulating and/or modulating factors.

It is advisable to carry out the control test simultaneously with the actual test. Further, it is important to use the same number of hybrid phagocyte cells, derived from the same phagocyte cell line in the control test and actual test. In this way, differences in quality, number and capacity of the phagocyte cells are eliminated such that the difference in measured results between both tests can only be attributed to factors in the fluid under analysis. Preferably, a chemiluminescent substrate such as luminol or lucigenine is further added to the hybrid phagocyte cells to intensify chemiluminescence. In this way, the measured results and consequently the differences between the actual test and the control test will become more significant.

The phenomena occurring can be illustrated in a simple way by means of reaction equations. Supposing e.g. that a stimulating factor or stimulator is present in the fluid to be analysed, the activation and light emission may be represented as follows:

$$M\phi + \text{stimulator} \rightarrow M\phi^* + CLP \rightarrow CL$$

wherein $M\phi$ and $M\phi^*$ are indications of the phagocyte cells in inactivated and activated state respectively, CLP represents the chemiluminescent substrate and CL represents the light emission. If the amount and capacity of the phagocyte cells, as well as the amount of chemiluminescent substrate is equal for the actual test and the control test, then it can be concluded easily that the degree of chemiluminescence is dependent from the presence of the stimulator and also dependent from the amount thereof.

Supposing that the chemiluminescence of the hybrid phagocyte cells is influenced not only by a stimulator but only by a modulating agent (modulator) which acts directly upon the phagocyte cells or upon the stimulator, then the following equation is obtained:

$$M\phi + \text{stimulator} + \text{modulator} \rightarrow M\phi^* + CLP \rightarrow CL$$

wherein the symbols have the aforesaid meanings. It can be concluded easily that if the amount and capacity of the phagocyte cells as well as the amount of stimulator and the amount of chemiluminescent substrate are equal for the actual test and the control test, the degree of chemiluminescence will directly by dependent from the presence of a modulator in the fluid to be analyzed and also dependent from the amount thereof.

Many practical embodiments are conceivable within the framework of the invented analyzing method. Some thereof will be treated in the following section of this description.

(a) Determination of opsonizing anti-bodies or of their corresponding antigens

If phagocyte cells are combined with a stimulator and with specific anti-bodies against that stimulator, a much stronger chemiluminescence than with utilisation of the stimulator alone is often obtained.

The phenomenon is occurring with several stimulators including bacteria (such as micrococci) and parasites (such as plasmodiums and tryponosomes) and may be represented by the following equation:

$$M\phi + \text{stimulator} + \text{IgG-anti-body} \rightarrow M\phi^* + CLP \rightarrow CL$$

wherein the symbols have the same meaning as before.

The phenomenon is presumably based upon "opsonisation" of the stimulator by the anti-bodies in preparation of phagocytosis. The stimulator particles are getting coated with anti-bodies and as soon as they come in the vicinity of a phagocyte cell, the anti-bodies will also adhere to the membrane of that phagocyte cell (at the Fc-receptor positions thereof). Thus, a link between the phagocyte cell and the stimulator particles is effected leading to activation of the phagocyte cell and eventually to phagocytosis. As a result, a stronger light emission than with utilisation of the stimulator alone is obtained.

This offers a possibility of detecting the presence of specific anti-stimulator anti-bodies and the proportion thereof in a biological fluid with the aid of certain stimulators (such as bacteria, parasites or other antigens). Inversely, this phenomenon offers a possibility to determine the presence of certain stimulators (such as bacteria or parasites) and their proportion in biological fluids by means of specific anti-bodies.

Since a stronger chemiluminescence will not occur when non-opsonizing anti-bodies are used, the phenomenon may also be utilized to detect a difference between opsonizing and non-opsonizing anti-bodies against the same stimulator serving as an antigen.

(b) Determination of complement

If phagocyte cells from a continuous cell line are combined with a stimulator and with complement (a certain immunological factor) then a much stronger chemiluminescence than with use of the stimulator alone is often obtained. This phenomenon will mostly occur when using a yeast extract from *Saccharomyces cerevisiae* and from certain yeasts (Candida's) as a stimulator. It may be represented as follows:

$$M\phi + \text{stimulator} + \text{complement} \rightarrow M\phi^* + CLP \rightarrow CL$$

wherein the symbols have the aforesaid meanings.

In other cases, an intensified chemiluminescence is only occurring if anti-bodies against the specific stimulator are added thereto. This is occurring mostly when using certain bacteria (e.g. Streptococci) as a stimulator. It may be represented as follows:

$$M\phi + \text{stimulator} + \text{IgG-anti-body} + \text{complement} \rightarrow M\phi^* + CLP \rightarrow CL$$

wherein the symbols have the aforesaid meanings.

Both phenomena are presumably based on opsonisation of the stimulator by the complement as present, without or with intermediance of the said anti-bodies, in preparation of phagocytosis. The stimulator particles are getting coated with complement and as soon as they come in the vicinity of a phagocyte cell, the complement will also adhere to the membrane of that phagocyte cell (at the C3b-receptor positions thereof). In this way, a link between the phagocyte cell and the stimulator particles is effected which will lead to phagocytosis, activation of the oxygen-redox-metabolism and eventually to chemiluminescence. As a result, a stronger light emission than with use of the stimulator alone is obtained.

This offers the possibility to determine the presence and also the proportion of complement in a biological fluid with the aid of certain stimulators (such a yeast extract or Streptococci) and, if necessary, anti-stimulator anti-bodies.

The inverse phenomenon, viz. the determination of a stimulator in biological fluids with the aid of complement, can be effected less easily. Determination of a stimulator such as yeast extract with the aid of complement alone is hardly possible because complement will react with several stimulators. Instead thereof, the chemiluminescence test may be used to effect a "screening" of several stimulators with the aid of complement. On the other hand, a qualitative or quantitative determination of stimulators such as Streptococci with the aid of complement and anti-bodies is well possible because the anti-bodies are specific to the stimulator in that case.

(c) Determination of inhibitors

It has appeared that the action of stimulators on the chemiluminescence of phagocyte cells is sometimes inhibited by certain factors in the biological fluids. Examples of such factors or inhibitors are: Fc fragments, C3 fragments, opsonizing immune complexes, natural or synthetic Fc peptides, anti-Fc anti-bodies and anti-C3-anti-bodies.

While for instance the light emission may be intensified by combining phagocyte cells with bacteria and with specific anti-bacteria anti-bodies, the light emission can be deintensified by combining phagocyte cells with bacteria and discrete Fc fragments (fragments of anti-bodies).

This offers a possibility to determine the presence and the proportion of such inhibitors in biological fluids. More than one control test will then be necessary, e.g. a test with the stimulator alone, a test with the stimulator and anti-bodies, a test with the stimulator and complement, etc. but this need not be an objection.

(d) Determination of membrane-specific anti-bodies

If phagocyte cells from a continuous cell line are combined with anti-bodies which react specifically to the membrane of such phagocyte cells (membrane-specific anti-bodies) then such anti-bodies will often have a stimulating activity on chemiluminescence.

This phenomenon may be represented as follows:

$$M\phi + \text{anti-}M\phi\text{-anti-bodies} \rightarrow M\phi^* + CLP \rightarrow CL$$

wherein the symbols have the aforesaid meanings.

Moreover, the same anti-bodies are often inhibitory to conventional chemiluminescence stimulators; this effect is shown when the phagocyte cells are combined with such stimulators and such anti-bodies.

These phenomena together offer a possibility for the qualitative and quantitative determination of anti-membrane-anti-bodies in biological fluids. Of course, at least two tests (with and without stimulator) are needed then. Further, the results seem to be dependent from the type of phagocyte cell line and this means that parallel tests with at least two different cell lines are desirable.

(e) Determination of membrane-specific lectins

Certain lectins with may act specifically to the membrane of the phagocyte cells (membrane-specific lectins) will also have a stimulating activity on the chemiluminescence thereof. The phenomenon can be represented as follows:

$$M\phi + \text{anti-membrane lectin} \rightarrow M\phi^* + CLP \rightarrow CL$$

wherein the symbols have the aforesaid meanings.

The stimulating activity of such lectins may be inhibited by certain substances such as monosaccharides.

This offers a possibility for the qualitative and quantitative determination of such lectins and of such monosaccharides in biological fluids.

(f) Determination of lymphokines

The phagocyte cells of a few cell lines will show only a weak chemiluminescence under influence of the conventional stimulators. However, if such phagocyte cells are incubated before hand with a so-called modulator, then they can often be stimulated to substantial luminescence by means of a conventional stimulator. Apparently, the modulator induces a modification in the phagocyte cell which results in a better response of the phagocyte cell to the stimulator.

The phenomenon may be represented as follows:

$$M\phi + \text{modulator} \rightarrow M\phi(r)$$

$$M\phi(r) + \text{stimulator} \rightarrow M\phi^* + CLP \rightarrow CL$$

wherein $M\phi(r)$ represents the reactive phagocyte cell and the other symbols have the aforesaid meanings.

All conventional stimulators are possible as a stimulator in this case. The modulator mostly comprises lymphokines, that is soluble immunological factors, supplied by activated lymphocytes and also by gamma-interferon.

The phenomenon offers a possibility for qualitative and quantitative determination of lymphokines and interferon in biological fluids. Further, it offers a possibility of monitoring analytically the various steps in the purification of lymphokine compositions or interferon compositions.

(g) Determination of endotoxins

Endotoxins, e.g. lipopolysaccharides, can also be used as a modulator. Thus, if phagocyte cells (which only show a weak chemiluminescence with a stimulator alone) are incubated beforehand with endotoxins and are combined next with a conventional stimulator, then substantial chemiluminescence is obtained.

The phenomenon may serve to determine endotoxins qualitatively and quantitatively in biological fluids. The test seems to be more sensible than conventional tests in this field such as Limulus Amebocyte Lysate test (LAL-test).

Further, the endotoxins sometimes have a synergistic and sometimes have an antagonistic activity on lymphokines. In other words: if phagocyte cells (which show only weak chemiluminescence with a stimulator alone) are incubated before hand with a mixture of lymphokines and endotoxins and are combined then with a stimulator, as intensified chemiluminescence is obtained in some cases and a desintensified chemiluminescence is obtained in other cases, dependent from the phagocyte cells line used.

The phenomenon of synergism or antagonism offers a possibility of distinguishing lymphokines and endotoxins from each other and of determining them separately in biological fluids. Of course, in that case, tests with more than one cell line will have to be effected.

(h) Determination of toxic substances

It has appeared that the modulating activity of lymphokines may be influenced by several toxic substances. Thus, if phagocyte cells from a phagocyte cell line are incubated first with a combination of lymphokines (or another modulator) and a toxic substance, and are combined next with a conventional stimulator, then the chemiluminescence is often weaker than in the case of using only the modulator and stimulator.

This phenomenon is shown by many chemical substances of toxic nature. Thus, it offers a possibility of determining toxic substances qualitatively and quantitatively in biological fluids. Further, it offers a possibility of toxicological screening of pharmaceutical compositions without using test animals.

It will be apparent that the above list of special cases may be supplemented with many others without passing beyond the limits of the invention. Thus, immune complexes and pharmaceutical triggers such as histamine may also be determined qualitatively and quantitatively in serum and other biological fluids.

Further, it will be apparent that the analyzing method of the invention may be utilized in the field of biotechnical, clinical, immunological and pharmacological search. Thus, the toxicological screening of pharmaceuticals seems to be a very important utilisation. During clinical searches (e.g. the detection of lymphokines or interferon) the invented analyzing method may lead to a certain indication about the nature of the disease, thus making the diagnosis easier. In the biotechnical field, the invented method of analysis may lead to a satisfying search strategy for detecting bacteria, yeasts and parasites. Other possibilities will be clear to an expert in the art.

Further, there is a possibility in principle to extend said method of analysis and its utilisations to cell lines derived from hepatocytes, fibroblasts and other cells, which are capable of producing oxygen metabolites and chemiluminescence.

The invented method of analysis is illustrated by the following non-restricting examples which also indicate possibilities for further utilisation.

EXAMPLE 2

Determination of epsonizing anti-bodies in a serum

In this example, the chemiluminescence of hybrid macrophage cells was measured after stimulation by micrococci with or without addition of an anti-micrococci anti-serum.

The macrophage cells belonged to the cell line 2C11-12 from table I. The micrococci belonged to *Micrococcus luteus* (available from Worthington Biochem. Corp., New Jersey). Prior to use; they were washed three times with a physiological saline solution, resuspended in physiological saline to a concentration of 4 mg/ml and stored at −70° C.

The anti-serum was prepared by injecting rabbits intravenously with 2 mg micrococci (12 injections distributed in 4 weeks), then bleeding the rabbits and collecting serum from the blood.

For effecting the tests the macrophage cells were transmitted from Petri-dishes to plastic cuvettes (PCT-cuvettes, Lumac 4960) in such a way that each cuvette contained 1 ml of cell suspension including $2 \times 10^4$ cells. Thereupon the cuvettes were incubated for 2-3 days. After incubation, the culture medium was removed and replaced by an equal amount of Veronal-buffered physiological saline which contained 8.3 g sodium chloride, 1.02 g sodium, 5,5-diethylbarbiturate, 102 mg $MgCl_2$, 22 mg $CaCl_2$, 200 mg beef serum albumine, 200 mg glucose and 3.5 ml 1N hydrochloric acid per liter. Further, 100 $\mu$l of 0.2 mM Luminol solution (Sigma Chemical Corp., St. Louis, Mo.) was added to each cuvette, as well as 200 $\mu$g micrococci and (in some tests) 10 $\mu$l of anti-micrococci anti-serum. The resulting mixture was tested on chemiluminescence in an apparatus of the Biolumat 9505 type (Laboratorium Prof. Dr. Berthold, Wildbad, German Federal Republic). The kinetics of the light emission were plotted in parallel experiments during a period of half an hour.

In the graphical representation of FIG. 1, the maximum light intensity of the macrophage cells during the tests has been expressed in CPM, i.e. counted photons per minute. It appears clearly that the micrococci-stimulated light emission is intensified by the anti-micrococci anti-serum which offers a possibility to detect the presence of opsonizing anti-micrococci anti-bodies in the anti-serum and to determine the proportion thereof.

Further, this test offers a possibility to detect the presence of micrococci in a serum and to determine the content thereof, since the anti-micrococci anti-serum in itself has no activating influence on macrophage cells and will cause no chemiluminescence without the presence of micrococci.

EXAMPLE 3

Determination of complement in a serum

In this example, the chemiluminescence of hybrid macrophage cells was measured after stimulation by yeast extract, with or without addition of a complement composition.

The macrophage cells belonged to the cell line 2C11-12 from table I. The yeast extract (Zymosan from Sigma Chem. Corp.) was an extract of *Saccharomyces cerevisiae*. Prior to use, it was boiled for 1 hour in a physiological cell line solution, then suspended in fresh physiological cell line, to reach a concentration of 25 mg/ml and stored at −70° C. The complement composition was a complement-containing cavia-serum (Behringwerke, Marburg, German Federal Republic).

The chemiluminescence tests were effected in the same way as in example 2, thereby using 50 $\mu$g yeast extract and (in some tests) 0.1 $\mu$l of complement composition per cuvette. The results expressed in terms of maximum light intensity, are represented in FIG. 2.

It appears from the results that the yeast extract-stimulated light emission of the macrophage cells is intensified by complement composition. This offers a possibility to detect the present of complement in blood serum and to determine the proportion thereof.

Inversely, the test offers a possibility to screen several stimulators on their reaction with complement.

EXAMPLE 4

Determination of lymphokines in biological fluids

In this example, the chemiluminescence of macrophage cells was measured after stimulation by yeast extract, with or without previous modulation by a lymphokine composition.

The macrophage cells belonged to the cell lines 2C11-D3 and 2C11-12 from table I. The stimulating yeast extract (Zymosan) was equal to that of example 3. The lymphokine composition (LK-SN) was prepared by culturing spleen cells of rats in a concentration of $5 \times 10^6$ per ml in a medium containing Concanavalin A (Con A, Sigma) in a final concentration of 1 $\mu$g/ml. After 48 hours, the culture fluid was harvested, centrifuged for 10 minutes at 1500 rpm and filtrated through a 0.2 $\mu$m filter.

For effecting the tests, the microphage cells were transmitted from Petri-dishes to cuvettes (PST-cuvettes, Lumac 4960) in such a way that 1 ml of cell suspension including $2 \times 10^4$ macrophage cells was present in each cuvette. Further, 0 μl or 50 μl or 100 μl of lymphokine composition was added to each cuvette whereupon the cuvettes were incubated for 2-3 days. After incubation, the culture medium was removed and replaced by an equal amount of Veronal-buffered physiological saline solution (the same as in example 2). Further, 100 μl 0.2 mM luminol solution and 50 μg yeast extract was added to each cuvette. The resulting mixtures were tested on chemiluminescence in a Biolumat 9505 apparatus. The kinetics of the light emission were plotted in parallel experiments during a period of half an hour.

In the graphical representation of FIG. 3, the maximum light intensity of the macrophage cells during the tests is shown. It appears from this figure that the macrophage cells are stimulated only to a slight degree by yeast extract alone and that they show a clear stimulation by yeast extract after previous incubation with lymphokine composition. Further, it appears that the light emission is dependent from the dosage of the lymphokine composition. This is an indication for the modulating activity of the lymphokine composition and offers a possibility for the qualitative and quantitative determination of lymphokines in biological fluids.

EXAMPLE 5

Determination of interferon in biological fluids

In this example, the chemiluminescence of macrophage cells was measured after stimulation by bacteria or yeast extracts, with or without previous incubation of the cells with an interferon composition.

The macrophage cells belonged to the cell line 2C11-D3 from table I. The same yeast extract (Zymosan) as in example 3 and the same micrococci as in example 2 were used for stimulation. The modulating interferon composition (a α-interferon-enriched serum indicated as IPN-α) was prepared by injecting mice intravenously with tuberculosis bacillae (BCG strain GL2) in a dosage of $5 \times 10^6$ bacillae per mg per 0.2 ml per mouse, and injecting them 2 weeks later intravenously with tuberculine (PPD, Instituut Pasteur van Brabant) in a dosage of 1 mg per 0.2 ml per mouse. Blood samples were taken, starting 4 hours after tuberculine injection, and serum was collected therefrom. The interferon titer of the serum was determined by a virus plaque diminution test, thereby using L-929 murine cells and vesicular stomatitis virus (VSV).

The tests were carried out in the same way as in example 4, the pre-incubation step therein being effected without any addition or with addition of 10 units or 1 unit of interferon composition. Stimulation was effected with 50 μg yeast extract or 200 μg micrococci. The results are shown in FIG. 4.

From the results, it appears that the light emission of macrophage cells stimulated by micrococci or yeast extract is intensified by previous incubation with an interferon composition and further, that the degree of intensification is clearly dependent from the dosage of the interferon composition. This offers a good possibility to detect the presence of interferon in biological fluids and further to determine the content thereof.

EXAMPLE 6

Determination of lymphokines or interferon in biological fluids

In this example, the chemiluminescence of macrophage cells was measured after stimulation by yeast extract, with or without previous incubation with a lymphokine composition or an interferon composition.

The macrophage cells belonged to the cell lines 2C11-12 and LA5-9 from table I. The yeast extract (Zymosan) was equal to that of example 3. The lymphokine composition (LK-SN) was equal to that of example 4 and the interferon composition (IFN-α) was equal to that of example 5. The chemiluminescence tests were carried out in the same way as in examples 4 and 5, the previous incubation step being effected without any addition or with addition of 50 μl lymphokine composition or 10 units of interferon composition. The stimulating yeast extract was used in an amount of 50 μg per cuvette. The results are shown in FIG. 5.

From the results, it appears that the light emission of both types of macrophage cells stimulated by yeast extract (Zymosan) is intensified by previous incubation with lymphokine composition or interferon composition. The macrophage cells from cell line 2C11-12 react stronger with the interferon composition and the macrophage cells from the cell line LA5-9 react stronger with the lymphokine composition from activated lymphocytes. This offers a possibility to detect the presence of lymphokine and interferon in biological fluids and to determine the proportion thereof, and further to make a distinction between lymphokines and interferon or rather to distinguish between lymphokines of different origin.

EXAMPLE 7

Determination of opsonizing anti-bodies in a serum

In this example, the chemiluminescence of hybrid macrophage cells was measured after stimulation by parasites (pathogenic protozoa), with or without addition of specific anti-parasite anti-bodies thereto.

(a) In a first test series, use was made of the parasite *Plasmodium chabaudi* (inducer of malaria) which is living in red blood cells (erythrocytes). Three types of stimulator were used, viz. a normal erythrocyte composition, an infected erythrocyte composition and an anti-plasmodium-anti-serum. The normal erythrocyte composition (indicated as ERY(N)) was obtained from the blood of healthy mice and contained $10^6$ red blood cells per 10 ul.

The infected erythrocyte composition (indicated as ERY(I)) was obtained by infecting mice with plasmodium, bleeding the mice and collecting red blood cells from the blood. Under a microscope, it appeared that 30–40 percent of the red blood cells were infected by plasmodiums. The anti-plasmodium anti-serum (indicated as anti-Pc) was obtained by bleeding mice which had survived an infection with *Plasmodium chabaudi* and collecting a serum from the blood.

The macrophage cells belonged to the cell line 2C11-12 from table I and were incubated before hand with a modulator for intensifying the contrast during light emission. The modulator was an interferon composition (IFN-γ) according to example 5 or a lymphokine composition (LK-SN) according to example 4.

The tests were carried out in the way of example 4, the previous incubation step being effected with the addition of 10 units interferon composition of 50 μl of lymphokine composition. Stimulation was effected with 1 μl normal erythrocyte composition or 1 μl infected erythrocyte composition, both with or without 1 μl anti-serum.

In the graphical representation of FIG. 6, the maximum light intensity of the macrophage cells during the tests (expressed in CPM) is shown. It appears that only the combination of plasmodium (infected erythrocytes) with anti-plasmodium anti-serum will stimulate an intense light emission, in clear contrast to plasmodiums alone or to a combination of antiserum with normal erythrocytes. The contrast is intensified by the modulator.

This offers a possibility of qualitatively and quantitatively determining anti-plasmodium anti-bodies, and if desired, plasmodiums themselves in blood.

(b) In a second test series, use was made of the parasite *Trypanosoma brucei* (inducer of sleeping sickness). This parasite has an extra cellular existence and therefore, no erythrocytes were needed.

Two compositions were used as stimulators, viz. a trypanosoma composition and and anti-serum. The trypanosoma composition (Tryp) contained $10^5$ cells per 1 μl and was obtained by bleeding infected mice and centrifuging the blood (the trypanosomae remain in the supernatant). The anti-serum (Anti-Tryp) was obtained by bleeding infected mice which had survived the trypanosoma infection and collecting an IgG-containing serum from the blood.

The macrophage cells belonged to the cell line LA5-9 from table 1 and were incubated before hand with a modulator comprising a lymphokine composition (LK-SN) equal to that of example 4, for intensifying the contrast.

The chemiluminescence tests were carried out in the way of example 4, the previous incubation being effected with addition of 50 μl lymphokine composition thereto. Stimulation was effected with 1 μl trypanosoma composition, with or without 1 μl anti-serum.

In the graphical representation of FIG. 6 (below), the maximum light intensity of the macrophage cells during the tests (expressed in CPM) is shown. It appears clearly that the light emission stimulated by trypanosomae is substantially intensified by the addition of an anti-trypanosoma anti-serum. A high contract is produced by the modulator used before hand.

This test offers a possibility for qualitative and quantitative determination of trypanosoma anti-bodies or of trypanosoma itself in blood.

EXAMPLE 8

Determination of membrane-specific anti-bodies

In this example, the chemiluminescence of hybrid macrophage cells was measured after stimulation by membrane-specific anti-bodies. Further, the chemiluminescence of hybrid macrophage cells was measured after stimulation by bacteria, with or without membrane-specific anti-bodies.

The macrophage cells belonged to the cell lines 2C11-12 and LA5-9 from table I. The membrane-specific anti-bodies were prepared by injecting macrophage cells from the cell lines 2C11-12 and LA5-9 into mice, bleeding the mice and collecting a serum containing specific anti-bodies (anti-2C11-12 and anti-LA5-9) in purified state from the blood. Further, an anti-serum without membrane-specific activity (indicated as IgG) was used as control.

The chemiluminescence tests were carried out in the way of example 2, the stimulation step being effected initially with one of the three anti-body compositions each time in an amount of 100 μg per cuvette.

After measurement of the stimulation by the anti-body compositions 200 μg micrococci (the same as in example 2) were added to each cuvette and the chemiluminescence was measured again.

The maximum light intensity of chemiluminescence during the first part of the tests is shown in the right-hand part of FIG. 7. It appears clearly that the membrane-specific anti-bodies have a stimulating activity on chemiluminescence with one of the cell lines and have hardly any influence with the other cell line.

The reduction of the maximum light intensity (with regard to the light emission generated by micrococci alone) has been shown in the left-hand part of FIG. 7. It appears that the membrane-specific anti-bodies have an inhibitory activity on the conventional stimulator (micrococci). Both phenomena together offer a possibility for qualitative and quantitative determination of membrane-specific anti-bodies in biological fluids.

EXAMPLE 9

Determination of endotoxins in biological fluids

In this example, the chemiluminescence of hybrid microphage cells was measured after stimulation by micrococci and after previous incubation with lymphokines, endotoxins or combinations thereof.

The macrophage cells belonged to the cell lines 2C11-12 and LA-9 from table I. Stimulation was effected with micrococci (the same as in EXAMPLE 2). A lymphokine composition (LK-SN) according to example 4 or an endotoxin composition (Lipopolysaccharide from Sigma Chem. Corp., indicated as LPS) was used as a modulator.

The chemiluminescence tests were carried out in the way of example 4, the stimulation being effected with 200 μg micrococci. The previous incubation was effected with 100 μl lymphokine composition of 10 μg lipopolysaccharide or a combination of both.

The maxiumum light intensity of the tests is shown in the graphical representation of FIG. 8. It appears clear that chemiluminescence is stimulated by the lymphokine composition and by the lipopolysaccharide as well. Further, it appears that a special effect is occurring when a combination of the lymphokine composition and lipopolysaccharide is used: light emission is synergistically intensified with the cell line 2C11-12 and antagonistically weakened with the cell line LA5-9.

These results offer a possibility for the qualitative and quantitative determination of lymphokines and endotoxins in biological fluids and a possibility to distinguish these factors from each other.

EXAMPLE 10

Determination of toxic substances

In this example, the chemiluminescence of hybrid macrophage cells was measure after stimulation with a conventional stimulator and previous incubation with lymphokines, whether or not in combination with a toxic substance.

The macrophage cells belonged to the cell line 2C11-12 from table I. A yeast extract (Zymosan) according to example 3 or Phorbol myristate acetate (PMA, Sigma Chem. Corp.) was used as a stimulator. Prior to use, the latter substance was dissolved in dimethyl sulfoxide to reach a concentration of 1 mg/ml and stored at −70° C.

A lymphokine composition (LK-SN) according to example 4 and an interferon composition (IFN-γ) according to example 5, as well as Lidocaine (Sigma Chem. Corp.) L77-57), a well-known anesthetic, were used as modulators.

The chemiluminescence tests were carried out in the way of example 4, stimulation being effected with 50 μg Zymosan or 10 μl PMA. The previous incubation was effected with 100 μl lymphokine composition or 10 units of interferon composition. After 3 days of incubation, 30 mmol Lidocaine was added to the composition of some tests. This Lidocaine was allowed to react for 10 minutes and was removed then by decanting.

The maximum light intensity during the tests is plotted in the graphical representation of FIG. 9. It appears clearly that the light emission intensified by previous incubation with a modulator is nearly completely suppressed by the addition of Lidocaine. This offers a possibility to detect Lidocaine and other toxic substances in biological fluids. Moreover, it offers a possibility of toxological screening of pharmaceutical substances.

It will be apparent that many variations to the embodiments described are possible with the frame work of the present invention.

What I claim is:

1. A method of producing continuous phagocyte cell lines, said method comprising a cell fusion between phagocytes and tumor cells suitable for cell fusion, followed by cloning and selecting the resulting hybrids, wherein the selection is effected on the basis of chemiluminescence properties.

2. The method of claim 1, wherein the tumer cells as used belong to a cell line C2E2-HAT which is a mutant of a murine lymphosarcomaderived cell line J 774.2.

3. A method of analyzing biological fluids, comprising the steps of: providing hybrid phagocyte cells belonging to a continuous phagocyte cell line, treating the hybrid phagocyte cells with a fluid to be analyzed, and measuring the chemiluminescence of the phagocyte cells thus treated in order to determine phagocyte-stimulating and/or phagocyte-modulating factors in the fluid under analysis.

4. The method as claimed in claim 3, wherein the chemiluminescence of phagocyte cells untreated with the fluid to be analysed is measured in a control test and wherein the measured results of the control test and the actual test are compared to determine the phagocyte-determining and/or phagocyte-modulating factors in the fluid under analysis.

5. The method of claim 4, wherein the control test is effected simultaneously with the actual test.

6. The method of claim 4, wherein an equal number of hybrid phagocyte cells belonging to the same phagocyte cell line is used in the control test and the actual test.

7. The method of claim 6, wherein a chemiluminescent substrate selected from the group consisting of luminol and lucigenin is added to the hybrid phagocyte cells for intensifying chemiluminescence.

8. The method of any one of claims 3-7, wherein a plurality of separate samples of the hybrid phagocyte cells are combined with a stimulator, at least one sample with and at least one sample without addition of the fluid to be analyzed, and wherein the presence and proportion of specific anti-stimulator anti-bodies, in the fluid under analysis, is determined by measurement of chemiluminescence and comparison of measured values.

9. The method of any one of claims 3-7, wherein a plurality of separate samples of the hybrid phagocyte cells are combined with a stimulator, at least one sample with and at least one sample without addition of the fluid to be analyzed, wherein the presence and proportion of specific anti-stimulator anti-bodies, in the fluid under analysis, is determined by measurements of chemiluminescence and comparison of measure value, and further wherein the stimulator is selected from the group consisting of micrococci, plasmodiums and trypanosomae.

10. The method of any one of claims 3-7, wherein a plurality of separate samples of the hybrid phagocyte cells are combined with anti-bodies against a stimulator, at least one sample with and at least one sample without addition of the fluid to be analyzed, and wherein the presence and proportion of said stimulator in the fluid under analysis is determined by measurement of chemiluminescence and comparison of measured values.

11. The method of any one of claims 3-7, wherein a plurality of separate samples of the hybrid phagocyte cells are combined with anti-bodies against a stimulator, at least one sample with and at least one sample without addition of the fluid to be analyzed, wherein the presence and proportion of said stimulator in the fluid under analysis is determined by measurement of chemiluminescence and comparison of measured values, and further wherein said stimulator is selected from the group consisting of micrococci, plasmodiums and trypanosomae.

12. The method of any one of claims 3-7, wherein a plurality of separate samples of the hybrid phagocyte cells are combined with a stimulator, at least one sample with and at least one sample without addition of the fluid to be analyzed, and wherein the presence and proportion of complement in the fluid under analysis is determined by measurement of chemiluminescence and comparison of measured values.

13. The method of any one of claims 3-7, wherein a plurality of separate samples of the hybrid phagocyte cells are combined with a stimulator, at least one sample with and at least one sample without addition of the fluid to be analysed, wherein the presence and proportion of complement in the fluid under analysis is determined by measurement of chemiluminescence and comparison of measured values, and further wherein the stimulator is selected from the group consisting of yeast extract and yeast.

14. The method of any one of claims 3-7, wherein a plurality of separate samples of the hybrid phagocyte cells are combined with a stimulator and with anti-stimulator anti-bodies, at least one sample with and at least one sample without addition of the fluid to be analyzed, and wherein the presence and proportion of complement in the fluid under analysis is determined by measurement of chemiluminescence and comparison of the measured values.

15. The method of any one of claims 3-7, wherein a plurality of sparate samples of the hybrid phagocyte cells are combined with a stimulator and with anti-stimulator anti-bodies, at least one sample with and at least one sample without addition of the fluid to be analyzed, wherein the presence and proportion of complement in the fluid under analysis is determined by measurement of chemiluminescence and comparison of the measured values, and further wherein the stimulator further comprises Streptococci.

16. The method of any one of claims 3–7, wherein a plurality of separate samples of the hybrid phagocyte cells are combined either with a stimulator or with a stimulator plus specific anti-stimulator anti-bodies, at least one sample of each with and at least one sample of each without addition of the fluid to be analyzed, and wherein the presence and proportion of inhibitory factors to the stimulator in the fluid under analysis is determined by measurement of chemiluminescence and comparison of the measured values.

17. The method of any one of claims 3–7, wherein a plurality of separate samples of the hybrid phagocyte cells are used either alone or with a stimulator, at least one sample with and a least one sample without addition of the fluid to be analyzed and wherein the presence and proportion of phagocyte cell membrane-specific antibodies in the fluid under analysis is determined by measurement of chemiluminescence and comparison of the measured values.

18. The method of any one of claims 3–7, wherein the hybrid phagocyte cells are combined with a stimulator after previous incubation or non-incubation with the fluid to be analyzed, and wherein the presence and proportion of a phagocyte-modulating factor in the fluid under analysis is determined by measurement of chemiluminescence and comparison of the measured values.

19. The method of any one of claims 3–7, wherein the hybrid phagocyte cells are combined with a stimulator after previous incubation or non-incubation with the fluid to be analyzed, wherein the presence and proportion of a phagocyte-modulating factor in the fluid under analysis is determined by measurement of chemiluminescence and comparison of the measured values, and further wherein the modulating factor is selected from the group consisting of lymphokines and interferon.

20. The method of any one of claims 3–7, wherein the hybrid phagocyte cells are combined with a stimulator after previous incubation or non-incubation with fluid to be analyzed, wherein the presence and proportion of a phagocyte-modulating factor in the fluid under analysis is determined by measurement of chemiluminescence and comparison of the measured values, and further wherein the modulating factor comprises endotoxins.

21. The method of any one of claims 3–7, wherein a plurality of separate samples of hybrid phagocyte cells of a first cell line are combined with a stimulator, at least one sample with and at least one sample without previous incubation with the fluid to be analyzed, wherein a plurality of separate samples of hybrid phagocyte cells of a second cell line are also combined with a conventional stimulator, at least one sample with and at least one sample without previous incubation with the fluid to be analyed, and wherein the presence and proportion of endotoxins in the fluid under analysis is determined by measurement of chemiluminescence and comparison of measured values.

22. The method of any one of claims 3–7, wherein a plurality of separate samples of the hybrid phagocyte cells are combined with a stimulator after previous incubation with a modulating agent, at least one sample with and at least one sample without addition of the fluid to be analyzed, and wherein the presence and proportion of toxic substances in the fluid under analysis is determined by measurement of chemiluminescence and comparison of measured values.

23. A method of toxicological screening of pharmaceuticals, comprising utilisation of the method of claim 22.

24. The method of any one of claims 3–7, wherein a plurality of separate samples of the hybrid phagocyte cells are combined with a stimulator after previous incubation with a modulating agents, at least one sample with and at least one sample without addition of the fluid to be analyzed, wherein the presence and proportion of toxic substances in the fluid under analysis is determined by measurement of chemiluminescence and comparison of measured values, and further wherein the modulating agent is selected from the group consisting of lymphokines and interferon.

25. A method of toxicological screening of pharmaceuticals, comprising utilisation of the method of claim 24.

* * * * *

UNITED STATES PATENT AND TRADEMARK OFFICE
CERTIFICATE OF CORRECTION

PATENT NO. : 4,737,455

DATED : April 12, 1988

INVENTOR(S) : Patrick De Baetselier

It is certified that error appears in the above-identified patent and that said Letters Patent is hereby corrected as shown below:

Column 1 Line 52 "ca" should read --can--.

Column 2 Line 23 "hydrids" should read --hybrids--.

Column 2 Line 24 "hydrid" should read --hybrid--.

Column 3 Line 42 "lumphokines" should read --lymphokines--.

Column 3 Line 51 "lateron" should read --later on--.

Column 4 Line 13 "suitble" should read --suitable--.

Column 4 Line 18 "Concanavaline" should read --Concanavalin--.

Column 4 Line 29 "single" should read --female--.

Column 4 Line 37 "8-azaquanine" should read --8-azaguanine--.

Column 5 Line 64 "Zynosan" should read --Zymosan--.

Column 7 Line 54 "by" should read --be--.

Column 8 Line 1 "tryponosomes" should read --trypanosomes--.

Column 9 Line 63 "with" should read --which--.

Column 10 Line 56 "as" should read --an--.

Column 10 Line 57 "desintensified" should read --deintensified--.

UNITED STATES PATENT AND TRADEMARK OFFICE
CERTIFICATE OF CORRECTION

PATENT NO. : 4,737,455

DATED : April 12, 1988

INVENTOR(S) : Patrick De Baetselier

It is certified that error appears in the above-identified patent and that said Letters Patent is hereby corrected as shown below:

Column 13 Line 41 "$\alpha$" should read -- $\gamma$ --.

Column 13 Line 42 "IPN-$\alpha$" should read --IFN-$\gamma$ --.

Column 14 Line 13 "$\alpha$" should read --$\gamma$ --.

Column 15 Line 11 "antiserum" should read --anti-serum--.

Column 15 Line 22 "and and" should read --and an--.

Column 16 Line 27 "microphage" should read --macrophage--.

Column 16 Line 32 "EXAMPLE" should read --example--.

Column 15 Line 43 "clear" should read --clearly--.

Column 17 Line 4 before "L77-57)" insert --(--.

Column 17 Claim 2 Line 34 "lymphosarcomaderived" should read --lymphosarcoma-derived--.

UNITED STATES PATENT AND TRADEMARK OFFICE
CERTIFICATE OF CORRECTION

PATENT NO. : 4,737,455

DATED : April 12, 1988

INVENTOR(S) : Patrick De Baetselier

It is certified that error appears in the above-identified patent and that said Letters Patent is hereby corrected as shown below:

Column 19 Line 41 Claim 20 delete "under" (second occurrence)

Column 20 Line 31 Claim 24 "agents" should read --agent--.

Signed and Sealed this

Fourteenth Day of February, 1989

*Attest:*

DONALD J. QUIGG

*Attesting Officer*         *Commissioner of Patents and Trademarks*